(12) United States Patent
McLaughlin et al.

(10) Patent No.: US 12,702,565 B2
(45) **Date of Patent: *Aug. 11, 2026**

(54) EXPANDABLE INTERVERTEBRAL IMPLANT

(71) Applicant: GLOBUS MEDICAL, INC., Audubon, PA (US)

(72) Inventors: Colm McLaughlin, Glenside, PA (US); Jason Zappacosta, Philadelphia, PA (US)

(73) Assignee: Globus Medical, Inc., Audubon, PA (US)

( * ) Notice: Subject to any disclaimer, the term of this patent is extended or adjusted under 35 U.S.C. 154(b) by 22 days.

This patent is subject to a terminal disclaimer.

(21) Appl. No.: 18/910,511

(22) Filed: Oct. 9, 2024

(65) Prior Publication Data

US 2025/0032271 A1 Jan. 30, 2025

Related U.S. Application Data

(63) Continuation of application No. 18/049,665, filed on Oct. 26, 2022, now Pat. No. 12,138,177, which is a (Continued)

(51) Int. Cl.
*A61F 2/44* (2006.01)
*A61B 17/86* (2006.01)
(Continued)

(52) U.S. Cl.
CPC ............ *A61F 2/4425* (2013.01); *A61B 17/86* (2013.01); *A61F 2/30749* (2013.01);
(Continued)

(58) Field of Classification Search
CPC .. A61F 2/4425; A61F 2002/443; A61F 2/445; A61F 2/447
See application file for complete search history.

(56) References Cited

U.S. PATENT DOCUMENTS 2,888,099 A 5/1959 Hoffmann
4,349,921 A 9/1982 Kuntz
(Continued)

FOREIGN PATENT DOCUMENTS

CA 2088066 A1 1/1992
DE 4012622 C1 7/1991
(Continued)

*Primary Examiner* — Anu Ramana

(57) ABSTRACT

An implant including first and second end plates, each of which defines at least one anterior ramped surface and at least one posterior ramped surface. A posterior actuator is positioned between the first and second end plates and has guiding ramp surfaces which correspond with the posterior ramped surfaces. An anterior actuator is positioned between the first and second end plates and guiding ramp surfaces which correspond with the anterior ramped surfaces. An actuator assembly extends between the posterior actuator and the anterior actuator and is configured to selectively move the posterior actuator and the anterior actuator simultaneously, move posterior actuator independently of the anterior actuator, or move the anterior actuator independently of the posterior actuator.

20 Claims, 8 Drawing Sheets

Related U.S. Application Data continuation of application No. 16/901,041, filed on Jun. 15, 2020, now Pat. No. 11,491,019, which is a continuation of application No. 15/808,180, filed on Nov. 9, 2017, now Pat. No. 10,709,569.

(51) Int. Cl.
*A61F 2/30* (2006.01)
*A61F 2/46* (2006.01)

(52) U.S. Cl.
CPC ............ *A61F 2/4455* (2013.01); *A61F 2/447* (2013.01); *A61F 2002/30261* (2013.01); *A61F 2002/30266* (2013.01); *A61F 2002/30329* (2013.01); *A61F 2002/30331* (2013.01); *A61F 2002/30365* (2013.01); *A61F 2002/30367* (2013.01); *A61F 2002/30405* (2013.01); *A61F 2002/30411* (2013.01); *A61F 2002/30433* (2013.01); *A61F 2002/30471* (2013.01); *A61F 2002/30507* (2013.01); *A61F 2002/30523* (2013.01); *A61F 2002/30537* (2013.01); *A61F 2002/30538* (2013.01); *A61F 2002/30556* (2013.01); *A61F 2002/30579* (2013.01); *A61F 2002/30593* (2013.01); *A61F 2002/30622* (2013.01); *A61F 2002/30624* (2013.01); *A61F 2/442* (2013.01); *A61F 2002/443* (2013.01); *A61F 2/4603* (2013.01); *A61F 2/4611* (2013.01); *A61F 2002/4625* (2013.01); *A61F 2002/4627* (2013.01)

(56) References Cited

U.S. PATENT DOCUMENTS 4,599,086 A 7/1986 Doty
4,863,476 A 9/1989 Shepperd
4,863,477 A 9/1989 Monson
5,123,926 A 6/1992 Pisharodi
5,290,312 A 3/1994 Kojimoto et al.
5,306,310 A 4/1994 Siebels
5,375,823 A 12/1994 Navas
5,390,683 A 2/1995 Pisharodi
5,522,899 A 6/1996 Michelson
5,534,030 A 7/1996 Navarro et al.
5,554,191 A 9/1996 Lahille et al.
5,571,192 A 11/1996 Schonhoffer
5,645,596 A 7/1997 Kim
5,653,763 A 8/1997 Errico et al.
5,665,122 A 9/1997 Kambin
5,676,701 A 10/1997 Yuan et al.
6,039,761 A 3/2000 Li et al.
6,045,579 A 4/2000 Hochschuler et al.
6,080,193 A 6/2000 Hochschuler et al.
6,099,531 A 8/2000 Bonutti
6,126,689 A 10/2000 Brett
6,176,882 B1 1/2001 Biedermann et al.
6,258,125 B1 7/2001 Paul et al.
6,554,863 B2 4/2003 Paul et al.
6,558,423 B1 5/2003 Michelson
6,562,074 B2 5/2003 Gerbec et al.
6,576,016 B1 6/2003 Hochschuler et al.
6,641,614 B1 11/2003 Wagner et al.
6,648,917 B2 11/2003 Gerbec et al.
6,666,891 B2 12/2003 Boehm, Jr. et al.
6,692,495 B1 2/2004 Zacouto
6,706,070 B1 3/2004 Wagner et al.
6,752,832 B2 6/2004 Ulrich
6,814,756 B1 11/2004 Michelson
6,830,589 B2 12/2004 Erickson
6,849,093 B2 2/2005 Michelson
6,852,129 B2 2/2005 Gerbec et al.
6,863,673 B2 3/2005 Gerbec et al.
6,881,228 B2 4/2005 Zdeblick et al.
7,018,415 B1 3/2006 McKay
7,070,598 B2 7/2006 Lim et al.
7,204,853 B2 4/2007 Gordon
7,217,291 B2 5/2007 Zucherman et al.
7,282,063 B2 10/2007 Cohen et al.
7,316,714 B2 1/2008 Gordon
7,473,276 B2 1/2009 Aebi et al.
7,547,325 B2 6/2009 Biedermann et al.
7,621,953 B2 11/2009 Braddock, Jr. et al.
7,641,693 B2 1/2010 Gutlin et al.
7,682,396 B2 3/2010 Beaurain et al.
7,749,270 B2 7/2010 Peterman
7,753,958 B2 7/2010 Gordon
7,771,473 B2 8/2010 Thramann
7,780,732 B2 8/2010 Abernathie
7,799,081 B2 9/2010 McKinley
7,815,683 B2 10/2010 Melkent et al.
7,837,734 B2 11/2010 Zucherman et al.
7,875,078 B2 1/2011 Wysocki et al.
7,901,409 B2 3/2011 Canaveral et al.
7,909,869 B2 3/2011 Gordon
7,951,199 B2 5/2011 Miller
7,985,256 B2 7/2011 Grotz et al.
8,062,375 B2 11/2011 Glerum
8,070,813 B2 12/2011 Grotz et al.
8,123,810 B2 2/2012 Gordon
8,137,405 B2 3/2012 Kostuik et al.
8,192,495 B2 6/2012 Simpson et al.
8,303,663 B2 11/2012 Jimenez et al.
8,377,140 B2 2/2013 DeFalco et al.
8,394,129 B2 3/2013 Lopez et al.
8,394,143 B2 3/2013 Grotz et al.
8,435,296 B2 5/2013 Kadaba et al.
8,454,695 B2 6/2013 Grotz et al.
8,597,360 B2 12/2013 McLuen et al.
8,647,386 B2 2/2014 Gordon
8,696,751 B2 4/2014 Ashley et al.
8,771,360 B2 7/2014 Jimenez et al.
8,894,710 B2 11/2014 Simpson et al.
8,932,355 B2 1/2015 Grotz et al.
8,940,049 B1 1/2015 JImenez et al.
8,956,413 B2 2/2015 Ashley et al.
8,992,620 B2 3/2015 Ashley et al.
9,028,550 B2 5/2015 Shulock et al.
9,358,123 B2 6/2016 McLuen et al.
9,358,125 B2 6/2016 JImenez et al.
9,445,919 B2 9/2016 Palmatier et al.
9,532,883 B2 1/2017 McLuen et al.
9,622,878 B2 4/2017 Grotz
9,750,618 B1 9/2017 Daffinson et al.
9,801,734 B1 10/2017 Stein et al.
9,987,146 B1 6/2018 Lentner et al.
10,022,239 B1 7/2018 Lentner et al.
10,219,915 B1 * 3/2019 Stein ....................... A61F 2/447
10,507,116 B2 * 12/2019 Shoshtaev ............. A61F 2/4425
11,224,522 B2 * 1/2022 To ......................... A61F 2/4455
11,285,018 B2 * 3/2022 Shoshtaev ............. A61F 2/4425
11,439,517 B2 * 9/2022 McLuen ................ A61F 2/447
2002/0045945 A1 4/2002 Liu
2002/0068976 A1 6/2002 Jackson
2002/0068977 A1 6/2002 Jackson
2003/0176926 A1 9/2003 Boehm et al.
2004/0030387 A1 2/2004 Landry et al.
2004/0049271 A1 3/2004 Biedermann
2004/0054412 A1 3/2004 Gerbec et al.
2004/0087947 A1 5/2004 Lim et al.
2004/0153065 A1 8/2004 Lim
2005/0021041 A1 1/2005 Michelson
2005/0021145 A1 1/2005 de Villiers et al.
2005/0033432 A1 2/2005 Gordon
2005/0080422 A1 4/2005 Otte et al.
2005/0113916 A1 5/2005 Branch
2005/0149188 A1 7/2005 Cook
2005/0171541 A1 8/2005 Boehm
2005/0251258 A1 11/2005 Jackson
2005/0273171 A1 12/2005 Gordon
2005/0273174 A1 12/2005 Gordon
2005/0278026 A1 12/2005 Gordon
2005/0283244 A1 12/2005 Gordon

(56) References Cited

U.S. PATENT DOCUMENTS

| | | | |
|---|---|---|---|
| 2005/0283245 | A1 | 12/2005 | Gordon |
| 2006/0004453 | A1 | 1/2006 | Bartish, Jr. et al. |
| 2006/0015184 | A1 | 1/2006 | Winterbottom et al. |
| 2006/0058878 | A1 | 3/2006 | Michelson |
| 2006/0084986 | A1 | 4/2006 | Grinberg et al. |
| 2006/0122701 | A1 | 6/2006 | Kister |
| 2006/0129244 | A1 | 6/2006 | Ensign |
| 2006/0142859 | A1 | 6/2006 | Mcluen |
| 2006/0149385 | A1 | 7/2006 | Mckay |
| 2006/0195192 | A1 | 8/2006 | Gordon et al. |
| 2006/0229729 | A1 | 10/2006 | Gordon |
| 2006/0241770 | A1 | 10/2006 | Rhoda et al. |
| 2006/0253201 | A1 | 11/2006 | Mcluen |
| 2007/0043442 | A1 | 2/2007 | Abernathie |
| 2007/0050030 | A1 | 3/2007 | Kim |
| 2007/0050032 | A1 | 3/2007 | Gittings et al. |
| 2007/0055377 | A1 | 3/2007 | Hanson et al. |
| 2007/0191951 | A1 | 8/2007 | Branch |
| 2007/0255415 | A1 | 11/2007 | Edie et al. |
| 2007/0270963 | A1 | 11/2007 | Melkent et al. |
| 2007/0270968 | A1 | 11/2007 | Baynham |
| 2008/0021559 | A1 | 1/2008 | Thramann |
| 2008/0065222 | A1 | 3/2008 | Hamada |
| 2008/0114467 | A1 | 5/2008 | Capote et al. |
| 2008/0140207 | A1 | 6/2008 | Olmos et al. |
| 2008/0147194 | A1 | 6/2008 | Grotz et al. |
| 2008/0161933 | A1 | 7/2008 | Grotz et al. |
| 2008/0167657 | A1 | 7/2008 | Greenhalgh |
| 2008/0183204 | A1 | 7/2008 | Greenhalgh et al. |
| 2008/0221694 | A1 | 9/2008 | Warnick et al. |
| 2008/0275455 | A1 | 11/2008 | Berry et al. |
| 2008/0281346 | A1 | 11/2008 | Greenhalgh et al. |
| 2008/0288073 | A1 | 11/2008 | Renganath et al. |
| 2008/0300598 | A1 | 12/2008 | Barreiro et al. |
| 2008/0306488 | A1 | 12/2008 | Altarac et al. |
| 2008/0319487 | A1 | 12/2008 | Fielding et al. |
| 2008/0319549 | A1 | 12/2008 | Greenhalgh et al. |
| 2009/0024217 | A1 | 1/2009 | Levy et al. |
| 2009/0062833 | A1 | 3/2009 | Song |
| 2009/0076616 | A1 | 3/2009 | Duggal et al. |
| 2009/0125062 | A1 | 5/2009 | Arnin |
| 2009/0149956 | A1 | 6/2009 | Greenhalgh et al. |
| 2009/0149959 | A1 | 6/2009 | Conner et al. |
| 2009/0204218 | A1 | 8/2009 | Richelsoph |
| 2009/0222100 | A1 | 9/2009 | Cipoletti et al. |
| 2009/0240334 | A1 | 9/2009 | Richelsoph |
| 2009/0270989 | A1 | 10/2009 | Conner et al. |
| 2009/0281628 | A1 | 11/2009 | Oglaza et al. |
| 2009/0292361 | A1 | 11/2009 | Lopez |
| 2009/0299478 | A1 | 12/2009 | Carls et al. |
| 2009/0312763 | A1 | 12/2009 | McCormack |
| 2010/0049324 | A1 | 2/2010 | Valdevit |
| 2010/0070041 | A1 | 3/2010 | Peterman |
| 2010/0082109 | A1 | 4/2010 | Greenhalgh et al. |
| 2010/0145455 | A1 | 6/2010 | Simpson et al. |
| 2010/0179657 | A1 | 7/2010 | Greenhalgh et al. |
| 2010/0211176 | A1 | 8/2010 | Greenhalgh |
| 2010/0222816 | A1 | 9/2010 | Gabelberger et al. |
| 2010/0286783 | A1 | 11/2010 | Lechmann et al. |
| 2011/0035011 | A1 | 2/2011 | Cain |
| 2011/0093074 | A1 | 4/2011 | Glerum et al. |
| 2011/0160861 | A1 | 6/2011 | Jimenez et al. |
| 2011/0172774 | A1 | 7/2011 | Varela |
| 2011/0276142 | A1 | 11/2011 | Niemiec et al. |
| 2011/0301713 | A1 | 12/2011 | Theofilos |
| 2011/0319997 | A1 | 12/2011 | Glerum et al. |
| 2012/0035729 | A1 | 2/2012 | Glerum et al. |
| 2012/0059470 | A1 | 3/2012 | Weiman |
| 2012/0059472 | A1 | 3/2012 | Weiman |
| 2012/0109308 | A1 | 5/2012 | Lechmann et al. |
| 2012/0130496 | A1 | 5/2012 | Duffield et al. |
| 2012/0165945 | A1 | 6/2012 | Hansell et al. |
| 2012/0185049 | A1 | 7/2012 | Varela |
| 2012/0209386 | A1 | 8/2012 | Triplett et al. |
| 2012/0215313 | A1 | 8/2012 | Saidha et al. |
| 2012/0226357 | A1 | 9/2012 | Varela |
| 2012/0265309 | A1 | 10/2012 | Glerum et al. |
| 2012/0277861 | A1 | 11/2012 | Steele et al. |
| 2012/0277870 | A1 | 11/2012 | Wolters et al. |
| 2012/0323329 | A1 | 12/2012 | Jimenez et al. |
| 2012/0330426 | A1 | 12/2012 | Mclaughlin et al. |
| 2013/0023993 | A1 | 1/2013 | Weiman |
| 2013/0023994 | A1 | 1/2013 | Glerum |
| 2013/0158663 | A1 | 6/2013 | Miller et al. |
| 2013/0158669 | A1 | 6/2013 | Sungarian et al. |
| 2013/0197642 | A1 | 8/2013 | Ernst |
| 2013/0197647 | A1 | 8/2013 | Wolters et al. |
| 2013/0211526 | A1 | 8/2013 | Alheidt et al. |
| 2013/0274883 | A1 | 10/2013 | McLuen et al. |
| 2014/0067071 | A1 | 3/2014 | Weiman et al. |
| 2014/0088714 | A1 | 3/2014 | Miller et al. |
| 2014/0163683 | A1 | 6/2014 | Seifert et al. |
| 2014/0243982 | A1 | 8/2014 | Miller |
| 2015/0018951 | A1 | 1/2015 | Loebl et al. |
| 2015/0066145 | A1 | 3/2015 | Rogers et al. |
| 2015/0088258 | A1 | 3/2015 | Jimenez et al. |
| 2015/0134064 | A1 | 5/2015 | Grotz et al. |
| 2015/0216676 | A1 | 8/2015 | Shulock et al. |
| 2015/0289988 | A1 | 10/2015 | Ashley et al. |
| 2015/0374508 | A1 | 12/2015 | Sandul |
| 2016/0166396 | A1 | 6/2016 | Mcclintock |
| 2016/0324654 | A1 | 11/2016 | Loebl et al. |
| 2016/0374826 | A1 | 12/2016 | Palmatier et al. |
| 2017/0100258 | A1 | 4/2017 | Jimenez et al. |
| 2017/0119543 | A1 | 5/2017 | Dietzel et al. |
| 2017/0296238 | A1 | 10/2017 | Snell et al. |
| 2017/0333196 | A1 | 11/2017 | Robinson |
| 2018/0036138 | A1 | 2/2018 | Robinson |
| 2018/0110629 | A1 | 4/2018 | Ewer et al. |
| 2019/0358057 | A1 | 11/2019 | McLaughlin |

FOREIGN PATENT DOCUMENTS

| | | | |
|---|---|---|---|
| DE | 4327054 | C1 | 4/1995 |
| EP | 0576379 | B1 | 6/1993 |
| EP | 0610837 | B1 | 7/1994 |
| EP | 3031424 | A1 | 6/2016 |
| EP | 3111896 | A1 | 1/2017 |
| FR | 2794968 | A1 | 12/2000 |
| JP | 2000-513263 | A | 10/2000 |
| JP | 2016-508412 | A | 3/2016 |
| JP | 2016-523678 | A | 8/2016 |
| JP | 2018-504245 | A | 2/2018 |
| KR | 200290058 | Y1 | 9/2002 |
| SU | 1424826 | A1 | 9/1988 |
| WO | 9201428 | A1 | 2/1992 |
| WO | 9525485 | A1 | 9/1995 |
| WO | 1999042062 | A1 | 8/1999 |
| WO | 1999066867 | A1 | 12/1999 |
| WO | 2002045625 | A1 | 6/2002 |
| WO | 2004019829 | A1 | 3/2004 |
| WO | 2004069033 | A2 | 8/2004 |
| WO | 2006045094 | A2 | 4/2006 |
| WO | 2006047587 | A2 | 5/2006 |
| WO | 2006113080 | A2 | 10/2006 |
| WO | 2008044057 | A1 | 4/2008 |
| WO | 2008134515 | A1 | 11/2008 |
| WO | 2009114381 | A1 | 9/2009 |
| WO | 2010103344 | A1 | 9/2010 |
| WO | 2012031267 | A1 | 3/2012 |
| WO | 2015009793 | A1 | 1/2015 |
| WO | 2016069796 | A1 | 5/2016 |
| WO | 2017040881 | A1 | 3/2017 |

* cited by examiner 250
100
178
118
110
116
190
156
150
136
130
170
138
190
176
200
200
250

250
110
118
113
116
158
111
240
180
225
220
210
178
176
190
170
230
215
136
100
138
150
156
190
131
133
130
250

190'
194
192
197
157'
150'
198
156'
162
160
160
152'

190'
194
157'
150'
192
156'
197
162
198
160
162
160
152'

190'
194
157'
150'
192
198
162
160
156'
160
152'

EXPANDABLE INTERVERTEBRAL IMPLANT

CROSS REFERENCE TO RELATED APPLICATIONS

This application is a continuation of U.S. patent application Ser. No. 18/049,665 filed on Oct. 26, 2022, which is a continuation of U.S. patent application Ser. No. 16/901,041, filed on Jun. 15, 2020, which is a continuation of U.S. patent application Ser. No. 15/808,180, filed on Nov. 9, 2017, all of which are incorporated by reference herein in their entirety for all purposes.

FIELD OF THE INVENTION

This present disclosure relates to stabilizing adjacent vertebrae of the spine by inserting an intervertebral implant, and more particularly an intervertebral implant that is adjustable in height and/or angularity and associated methods.

BACKGROUND

Bones and bony structures are susceptible to a variety of weaknesses that can affect their ability to provide support and structure. Weaknesses in bony structures have numerous potential causes, including degenerative diseases, tumors, fractures, and dislocations. Advances in medicine and engineering have provided doctors with a plurality of devices and techniques for alleviating or curing these weaknesses.

In some cases, the spinal column requires additional support in order to address such weaknesses. One technique for providing support is to insert a spacer between adjacent vertebrae.

SUMMARY

To meet this and other needs, expandable implants, systems, and methods are provided. The expandable implant may be expandable and adjustable in height and/or angularity. The implant may be inserted into an intervertebral disc space at a minimized height, and then expanded axially to restore height loss in the disc space. The implant may provide distraction as well as achieving optimal height restoration. The implant may also change in lordotic angulation independently from its expansion. This independent expansion and lordotic angulation may solve some of the problems currently encountered, such as excessive impaction during insertion, visual obstruction, and imperfect matching with patient's lordosis due to discrete increments in lordotic angulation. It will be appreciated that although generally described with respect to lordotic angulation, the implant may also be configured to provide kyphotic expansion and angulation to treat kyphosis as well.

In at least one embodiment, the present disclosure provides an implant for therapeutically separating bones of a joint. The implant includes a first end plate extending between an anterior end and a posterior end. The first end plate has a bone engaging surface, at least one anterior ramped surface and at least one posterior ramped surface on a side opposite the bone engaging surface. A second end plate extends between an anterior end and a posterior end. The second end plate has a bone engaging surface, at least one anterior ramped surface and at least one posterior ramped surface on a side opposite the bone engaging surface. A posterior actuator is positioned between the first and second end plates and has a corresponding number of first guiding ramp surfaces configured to be positioned opposite the at least one first end plate posterior ramped surface and a corresponding number of second guiding ramp surfaces configured to be positioned opposite the at least one second end plate posterior ramped surface. A pivot member is pivotally connected to each first guiding ramp surface and in sliding engagement with the respective at least one first plate posterior ramped surface and a pivot member is pivotally connected to each second guiding ramped surface and in sliding engagement with the respective at least one first plate posterior ramped surface. An anterior actuator is positioned between the first and second end plates and has a corresponding number of third guiding ramp surfaces configured to be positioned opposite the at least one first end plate anterior ramped surface and a corresponding number of fourth guiding ramp surfaces configured to be positioned opposite the at least one second end plate anterior ramped surface. A pivot member is pivotally connected to each third guiding ramp surface and in sliding engagement with the respective at least one first plate anterior ramped surface and a pivot member is pivotally connected to each fourth guiding ramped surface and in sliding engagement with the respective at least one first plate anterior ramped surface. An actuator assembly extends between the posterior actuator and the anterior actuator and is configured to selectively move the posterior actuator and the anterior actuator simultaneously, move posterior actuator independently of the anterior actuator, or move the anterior actuator independently of the posterior actuator.

In at least one embodiment, the present invention provides an implant including a first end plate extending between an anterior end and a posterior end. The first end plate defines at least one anterior ramped surface and at least one posterior ramped surface. A second end plate extends between an anterior end and a posterior end and defines at least one anterior ramped surface and at least one posterior ramped surface. A posterior actuator is positioned between the first and second end plates and has a corresponding number of first guiding ramp surfaces configured to be positioned opposite the at least one first end plate posterior ramped surface and a corresponding number of second guiding ramp surfaces configured to be positioned opposite the at least one second end plate posterior ramped surface. A pivot member is pivotally connected to each first guiding ramp surface and in sliding engagement with the respective at least one first plate posterior ramped surface and a pivot member is pivotally connected to each second guiding ramped surface and in sliding engagement with the respective at least one first plate posterior ramped surface. An anterior actuator is positioned between the first and second end plates and has a corresponding number of third guiding ramp surfaces configured to be positioned opposite the at least one first end plate anterior ramped surface and a corresponding number of fourth guiding ramp surfaces configured to be positioned opposite the at least one second end plate anterior ramped surface. A pivot member is pivotally connected to each third guiding ramp surface and in sliding engagement with the respective at least one first plate anterior ramped surface and a pivot member is pivotally connected to each fourth guiding ramped surface and in sliding engagement with the respective at least one first plate anterior ramped surface. An actuator assembly extends between the posterior actuator and the anterior actuator. The actuator assembly includes an actuator screw extending between a posterior end and an anterior end with a first external thread set proximate the posterior end and a second external thread set proximate the anterior end wherein the first and second external thread sets are oppositely handed. The posterior end of the actuator screw extends through and threadably engages a through passage in the posterior actuator. The actuator assembly further includes an actuator nut extending between a posterior end and an anterior end with a through passage extending from the posterior end to the anterior end and defining an internal thread within the through passage. The internal thread is threadably engaged with the second set of external threads. The actuator nut extends through the anterior actuator such that the actuator nut is axially fixed relative to the anterior actuator but rotatable relative thereto. Rotation of the actuator screw while the actuator nut does not rotate causes the posterior actuator and the anterior actuator to move simultaneously, rotation of the actuator screw and the actuator nut together causes the posterior actuator to move independently of the anterior actuator, and rotation of the actuator nut while the actuator screw does not rotate causes the anterior actuator to move independently of the posterior actuator.

In at least one embodiment, the implant may include one or more bearings. The bearings may be configured to connect one or both of the end plates to the actuator assembly and allow the actuator screw to rotate regardless of end plate angulation. For example, the posterior end of the actuator screw may include a ball which is supported in a spherical bearing supported by the first and second end plates. In an alternative arrangement, the implant may be provided without bearings present, such that the end plates would be free to pivot or translate without restriction.

In at least one embodiment, the disclosure provides a method of fusing adjacent vertebral bodies including inserting an implant defining a longitudinal axis extending between distal and proximal ends between bones of the joint, the implant includes a first end plate extending between an anterior end and a posterior end. The first end plate has a bone engaging surface, at least one anterior ramped surface and at least one posterior ramped surface on a side opposite the bone engaging surface. A second end plate extends between an anterior end and a posterior end. The second end plate has a bone engaging surface, at least one anterior ramped surface and at least one posterior ramped surface on a side opposite the bone engaging surface. A posterior actuator is positioned between the first and second end plates and has a corresponding number of first guiding ramp surfaces configured to be positioned opposite the at least one first end plate posterior ramped surface and a corresponding number of second guiding ramp surfaces configured to be positioned opposite the at least one second end plate posterior ramped surface. A pivot member is pivotally connected to each first guiding ramp surface and in sliding engagement with the respective at least one first plate posterior ramped surface and a pivot member is pivotally connected to each second guiding ramped surface and in sliding engagement with the respective at least one first plate posterior ramped surface. An anterior actuator is positioned between the first and second end plates and has a corresponding number of third guiding ramp surfaces configured to be positioned opposite the at least one first end plate anterior ramped surface and a corresponding number of fourth guiding ramp surfaces configured to be positioned opposite the at least one second end plate anterior ramped surface. A pivot member is pivotally connected to each third guiding ramp surface and in sliding engagement with the respective at least one first plate anterior ramped surface and a pivot member is pivotally connected to each fourth guiding ramped surface and in sliding engagement with the respective at least one first plate anterior ramped surface. An actuator assembly extends between the posterior actuator and the anterior actuator and is configured to selectively move the posterior actuator and the anterior actuator simultaneously, move posterior actuator independently of the anterior actuator, or move the anterior actuator independently of the posterior actuator. The method further includes actuating the actuator assembly after the implant is inserted to move the first and second end plates relative to one another to increase or decrease the lordotic angle or to move the first and second endplates farther apart to separate bones of the joint.

BRIEF DESCRIPTION OF THE DRAWINGS

The accompanying drawings, which are included to provide a further understanding of the present disclosure, are incorporated in and constitute a part of this specification, illustrate aspects of the present disclosure and together with the detailed description serve to explain the principles of the present disclosure. No attempt is made to show structural details of the present disclosure in more detail than may be necessary for a fundamental understanding of the present disclosure and the various ways in which it may be practiced. In the drawings.

DETAILED DESCRIPTION

Figure 1:
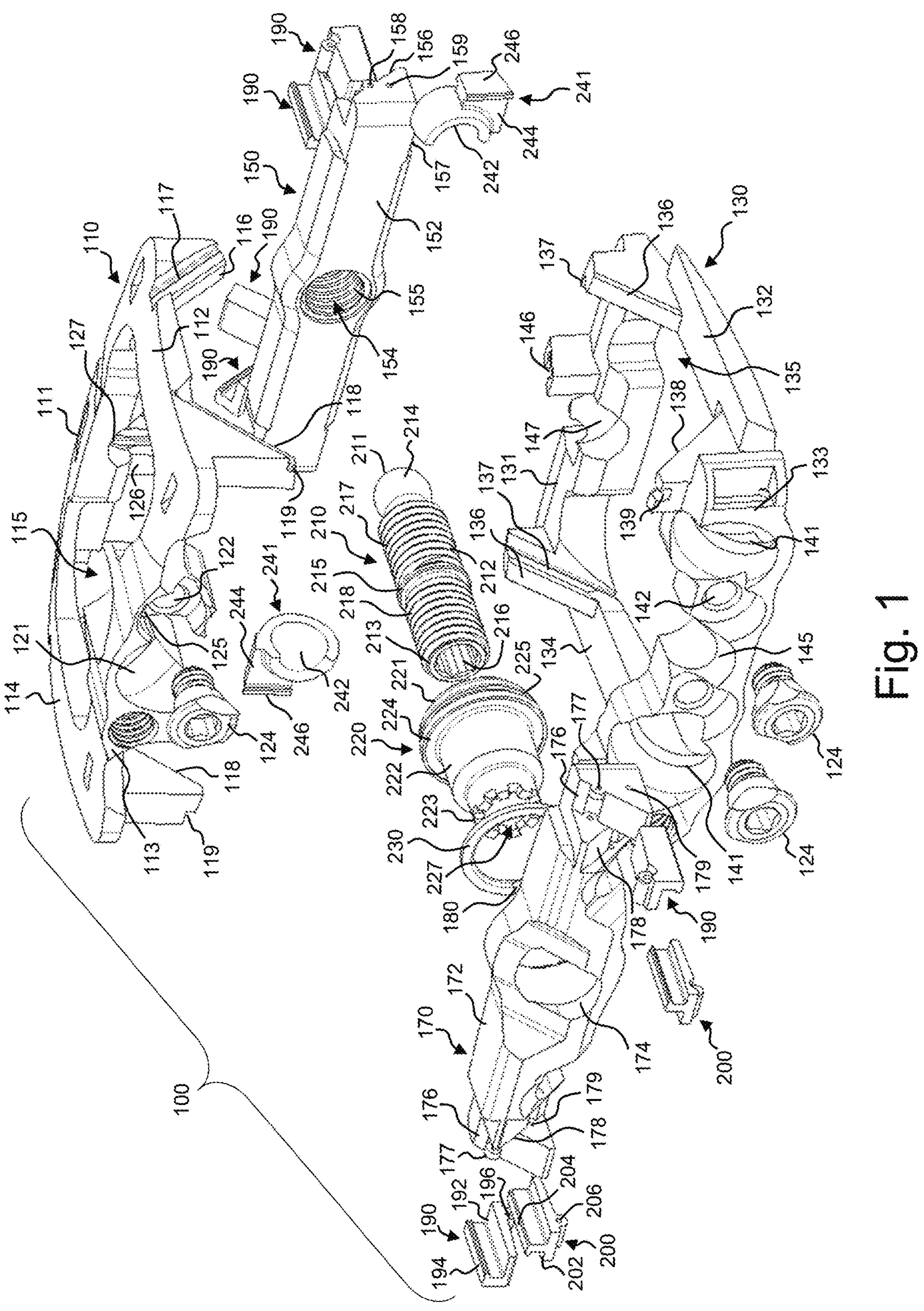
FIG. 1 is an exploded perspective view of an implant in accordance with an embodiment of the disclosure.

The aspects of the present disclosure and the various features and advantageous details thereof are explained more fully with reference to the non-limiting aspects and examples that are described and/or illustrated in the accompanying drawings and detailed in the following description.

It should be noted that the features illustrated in the drawings are not necessarily drawn to scale, and features of one aspect may be employed with other aspects as the skilled artisan would recognize, even if not explicitly stated herein. Descriptions of well-known components and processing techniques may be omitted so as to not unnecessarily obscure the aspects of the present disclosure. The examples used herein are intended merely to facilitate an understanding of ways in which the present disclosure may be practiced and to further enable those of skill in the art to practice the aspects of the present disclosure. Accordingly, the examples and aspects herein should not be construed as limiting the scope of the present disclosure, which is defined solely by the appended claims and applicable law. Moreover, it is noted that like reference numerals represent similar parts throughout the several views of the drawings.

The terms "a" or "an", as used herein, are defined as one or more than one. The term plurality, as used herein, is defined as two or more than two. The term another, as used herein, is defined as at least a second or more. The terms "including" and "having," as used herein, are defined as comprising (i.e., open language).

Implants of the disclosure allow for insertion into the intervertebral disc space at a minimized height and then expansion axially to restore height loss in the disc space. Implants of the disclosure allow continuous expansion and retraction within a range of expansion as well as achieving optimal height restoration. Implants of the disclosure may also change in lordotic angulation independently from its expansion. Implants of the disclosure may be utilized to minimize impaction during insertion, visual obstruction, and imperfect matching with a patient's lordosis due to discrete increments in lordotic angulation. Additionally, implants of the disclosure may also be collapsed and repositioned, as therapeutically indicated for the patient.

Referring to FIGS. 1-5 and 7-13, an implant 100 in accordance with an embodiment of the disclosure will be described. The implant 100 is operative, when positioned between adjacent bones of a joint, such as for example vertebrae (not shown), to stabilize a joint formed by adjacent vertebrae. The implant 100 is illustrated in an anterior interbody spacer configuration but it could also be used in other approaches, for example, such as direct lateral where coronal deformity is encountered.

Figures 2, 3:
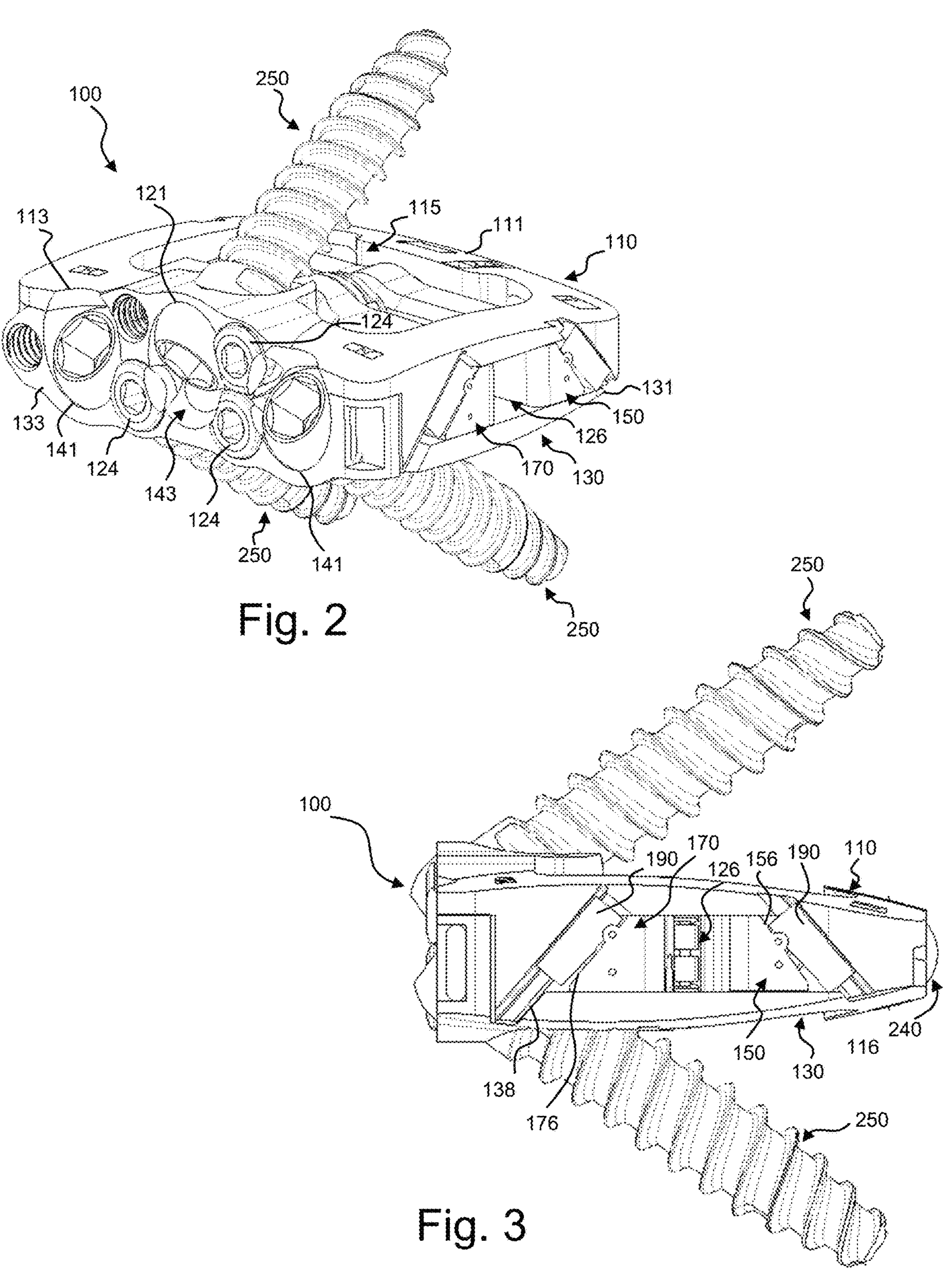
FIG. 2 is a perspective view of the implant of FIG. 1 in a compressed or reduced height configuration, together with three mounted bone screws.
FIG. 3 is a side elevation view of the implant as shown in FIG. 2.

With reference to FIGS. 1-3, the implant 100 generally includes upper and lower endplates 110, 130, anterior and posterior actuators 150, 170, actuator pivot members 190, 200, an actuator screw 210, an actuator nut 220, a spherical bearing 240 and a thrust washer 230. In addition, the implant may include a plurality of blocking screws 124 on the endplates 110, 130 to prevent migration of the fixation screws or anchors.

The upper end plate 110 includes a posterior rail 111 and an anterior rail 113 extending between opposed side rails 112, 114. The rails 111-114 extend about a through passage 115 into a graft chamber 128 within the implant. The passage 115 allows graft material or other therapeutically beneficial material to packed into or grow into the graft chamber 128. The upper end plate 110 defines a posterior guide ramp 116 along each side rail 112, 114 and an anterior guide ramp 118 along each side rail 112, 114. Each posterior guide ramp 116 defines a groove 117 configured to receive a portion of a respective pivot member 190 and each anterior guide ramp 118 defines a groove 117 configured to receive a portion of a respective pivot member 190. As will be described hereinafter, the pivot members 190 are pivotally connected to respective actuators 150, 170 and slide along the respective ramp 116, 118 as the plates 110, 130 expand or contract.

The anterior rail 113 defines at least one bone screw/anchor through hole 121, with one such hole 121 shown in the illustrated embodiment. A blocking screw hole 122 is positioned next to the through hole 121 and is configured to receive a blocking screw 124 which may be utilized to maintain the bone screw 250 or bone anchor 260 in the through hole 121. It will be appreciated that the bone screw 250 and bone anchor 260 may be used interchangeably in the respective hole 121 and may also be substituted with any other suitable fasteners. The anterior rail 113 also defines a first hemispherical portion 125 of a driver opening 143 as shown in FIG. 2. The posterior rail 111 defines a first hemispherical portion 127 of a seat for the spherical bearing 240, as will be described hereinafter. A receiving slot 126 extends next to the hemispherical portion 127 and is configured to receive a flange 246 of one of the bearing members 241 that defines a portion of the spherical bearing 240.

The lower end plate 130 includes a posterior rail 131 and an anterior rail 133 extending between opposed side rails 132, 134. The rails 131-134 extend about a through passage 135 into the graft chamber 128 within the implant. The passage 135 again allows graft material or other therapeutically beneficial material to packed into or grow into the graft chamber 128. The lower end plate 130 defines a posterior guide ramp 136 along each side rail 132, 134 and an anterior guide ramp 138 along each side rail 132, 134. The guide ramps 136 and 138 are laterally inward of the ramps 116, 118 such that the ramps 116, 118 may overlap the ramps 136, 138. Each posterior guide ramp 136 defines a groove 137 configured to receive a portion of a respective pivot member 190 and each anterior guide ramp 138 defines a groove 137 configured to receive a portion of a respective pivot member 200. As will be described hereinafter, the pivot members 190, 200 are pivotally connected to respective actuators 150, 170 and slide along the respective ramp 136, 138 as the plates 110, 130 expand or contract.

The anterior rail 133 defines at least one bone screw/anchor through hole 141, with two such holes 141 shown in the illustrated embodiment. A blocking screw hole 142 is positioned next to each through hole 141 and is configured to receive a blocking screw 124 which may be utilized to maintain the bone screw 250 or bone anchor 260 in the through hole 141. It will be appreciated that the bone screw 250 and bone anchor 260 may be used interchangeably in the respective holes 141 and may also be substituted with any other suitable fasteners. The anterior rail 133 also defines the second hemispherical portion 145 of the driver opening 143 as shown in FIG. 2. The posterior rail 131 defines the second hemispherical portion 147 of the seat for the spherical bearing 240. A receiving slot 146 extends next to the hemispherical portion 127 and is configured to receive a flange 246 of the other of the bearing members 241 that defines another portion of the spherical bearing 240.

Although anterior rails 113, 133 are shown with through holes 121, 141 configured to receive respective fasteners, it will be appreciated by one skilled in the art that the bore holes or through holes 121, 141 may be present in any suitable number and configuration for fixation. In the alternative, the bore holes or through holes 121, 141 may be omitted to provide a standalone device.

Figures 6, 7:
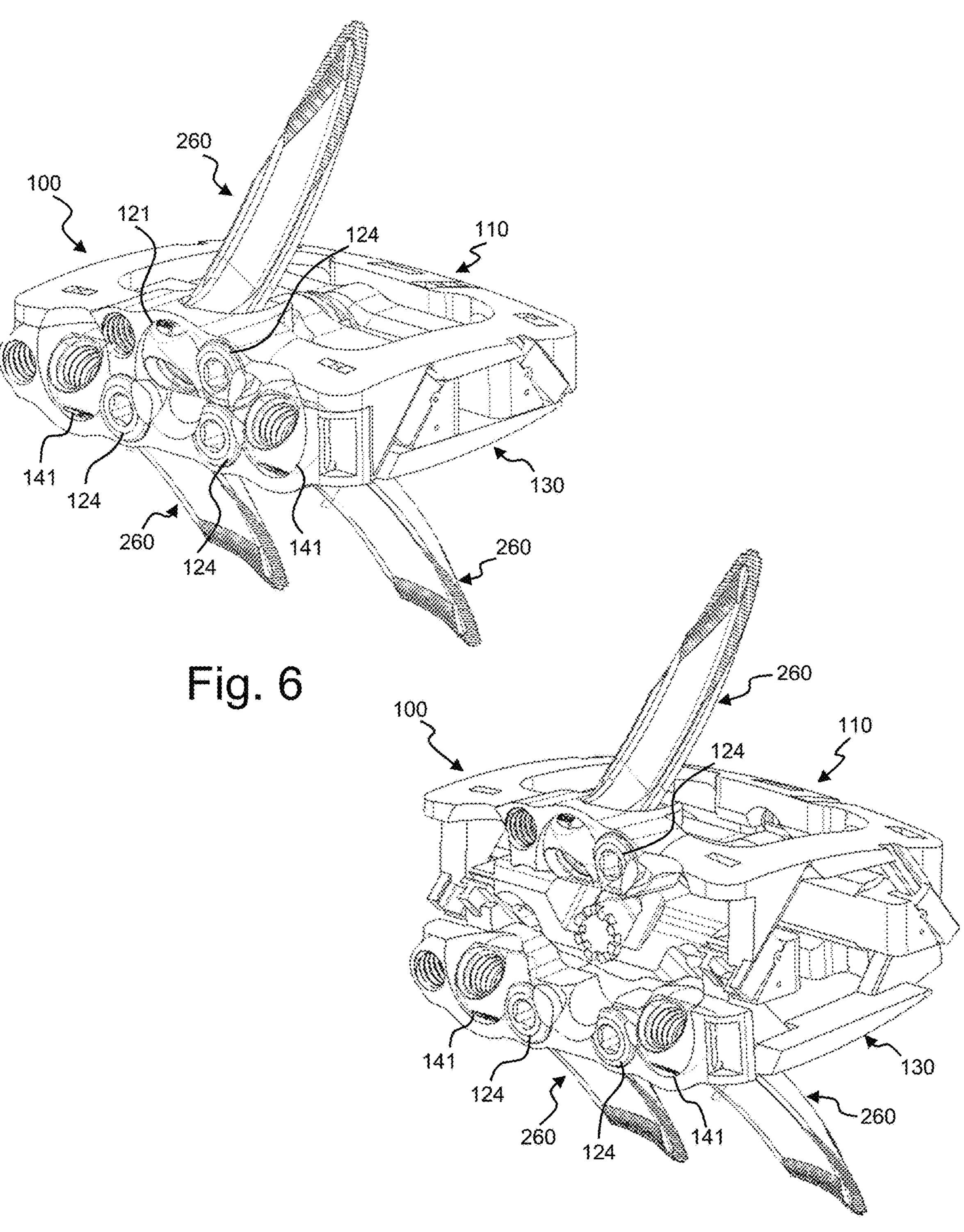
FIG. 6 is a perspective view of the implant of FIG. 1 in a compressed or reduced height configuration, together with three mounted bone anchors.
FIG. 7 is a perspective view of the implant of FIG. 1 in an expanded or increased height configuration, together with three mounted bone anchors.

While not shown, one or both of the end plates 110, 130 can be provided with teeth or other projections which can penetrate body tissue to reduce a likelihood of migration of implant 100 after implantation. Additionally, one or both of the end plates 110, 130 may be coated with or impregnated with therapeutic agents, including bone growth, healing, antimicrobial, or drug materials, which may be released at a therapeutic rate, using methods known to those skilled in the art. Additionally, while FIGS. 2-5 show bone screws 260 extending through the through holes 121, 141 for securing of the implant 100, the disclosure is not limited to such. For example, FIGS. 6 and 7 illustrate bone anchors 260 extending through the through holes 121, 141. Other anchoring elements may also be utilized. In each case, the through holes 121, 141 may have a concave opening such that the screws 250 or anchors 260 may be inserted into body tissue at an optimal angle with respect to implant 100, whereby optimal purchase may be obtained, or certain body tissue may be avoided.

Figures 4, 5:
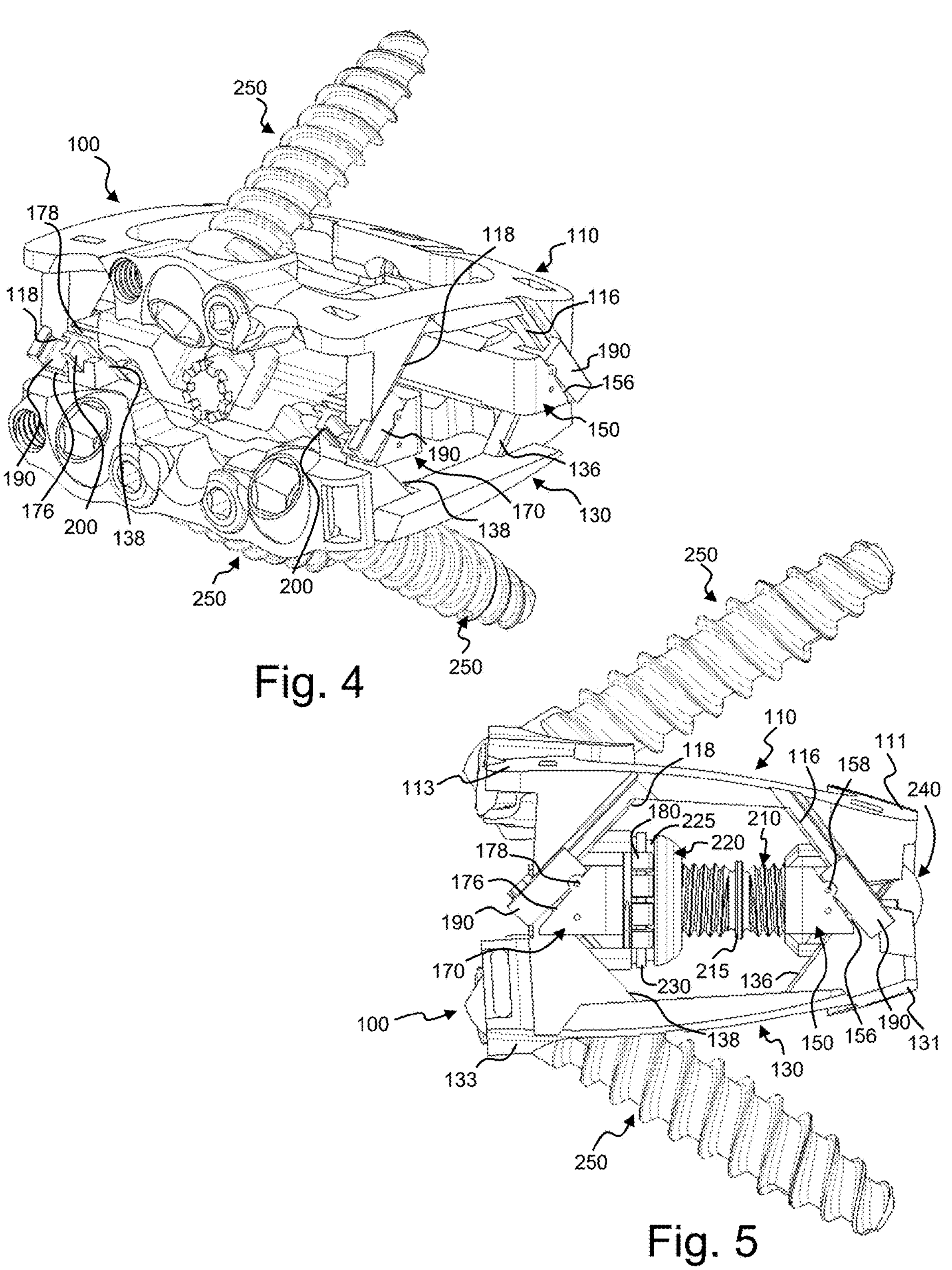
FIG. 4 is a perspective view of the implant of FIG. 1 in an expanded or increased height configuration, together with three mounted bone screws.
FIG. 5 is a side elevation view of the implant as shown in FIG. 4.

Implant 100 has a collapsed state or height, illustrated in FIGS. 2 and 3, and an expanded state or height, illustrated in FIGS. 4 and 5. Implants 100 of the disclosure may be inset into the intervertebral disc space at a collapsed height, and then expand axially (superior/inferior) to restore height loss in the disc space. The implant provides distraction as well as achieves optimal height restoration. When inserted in a collapsed state, implants 100 reduce impaction to tissue in the joint space during insertion, and form the least visually blocking or obstructing profile. Additionally, the lordotic angle of implant 100 may be adjusted to have an increased lordotic angle, illustrated in FIGS. 8 and 9, or a decreased lordotic angle, illustrated in FIGS. 10 and 11.

The anterior and posterior actuators 150, 170 are positioned between the plates 110, 130 and are moveable relative to the plates 110, 130 to control the separation between the plates 110, 130. The anterior actuator 150 is positioned between the plates 110, 130 proximate the anterior rails 111, 131. The anterior actuator 150 has a laterally extending body 152 with a central through passage 154 with internal threads 155 configured to threadably engage the actuator screw 210, as will be described hereinafter. An upper plate guiding ramp 156 is defined at each end of the body 152 and is configured to align with a respective anterior ramp 116 of the upper plate 110. Each of the upper plate guiding ramps 156 extends at the same incline angle as the opposing anterior ramp 116. Similarly, a lower plate guiding ramp 157 is defined inward of each end of the body 152 and is configured to align with a respective anterior ramp 136 of the lower plate 130. Each of the lower plate guiding ramps 157 extends at the same incline angle as the opposing anterior ramp 136. The body 152 defines pivot pin holes 158, 159 next to the guiding ramps 156, 157, respectively, for pivotal mounting of the pivot members 190.

The posterior actuator 170 is positioned between the plates 110, 130 proximate the posterior rails 113, 133. The anterior actuator 170 has a laterally extending body 172 with a central non-threaded through passage 174 configured to receive the actuator nut 220. A series of fingers 180 extend from the posterior side of the body 172 about the through passage 174 and are configured to engage and retain the actuator nut 220, as will be described hereinafter. An upper plate guiding ramp 176 is defined at each end of the body 172 and is configured to align with a respective posterior ramp 118 of the upper plate 110. Each of the upper plate guiding ramps 176 extends at the same incline angle as the opposing superior ramp 118. Similarly, a lower plate guiding ramp 177 is defined inward of each end of the body 172 and is configured to align with a respective superior ramp 138 of the lower plate 130. Each of the lower plate guiding ramps 177 extends at the same incline angle as the opposing superior ramp 138. The body 172 defines pivot pin holes 178, 179 next to the guiding ramps 176, 177, respectively, for pivotal mounting of the pivot members 190, 200.

Referring to FIG. 1, each of the pivot members 190 includes a guide surface 192 configured to engage and slide along a respective ramp 116, 118, 136. A groove engaging flange 194 extends from each guide surface 192 and is configured to engage within the respective ramp groove 117, 119, 137 to prevent separation from the respective ramp 116, 118, 136. The opposite side of each guide surface 192 defines a pivot slot 196 configured to align with respective pivot pin holes 158, 159, 178 such that a pivot pin (not shown) pivotally connects each pivot member 190 to a respective actuator 150, 170. The pivot members 200 are similar to the pivot members 190 and includes a guide surface 202 configured to engage and slide along a respective ramp 138. A groove engaging flange 204 extends from each guide surface 202, more centrally compared to the pivot member 190, and is configured to engage within the respective ramp groove 139 to prevent separation from the respective ramp 138. The opposite side of each guide surface 202 defines a pivot slot 206 configured to align with respective pivot pin holes 179 such that a pivot pin (not shown) pivotally connects each pivot member 200 to a respective actuator 170.

Figures 14, 15, 16:
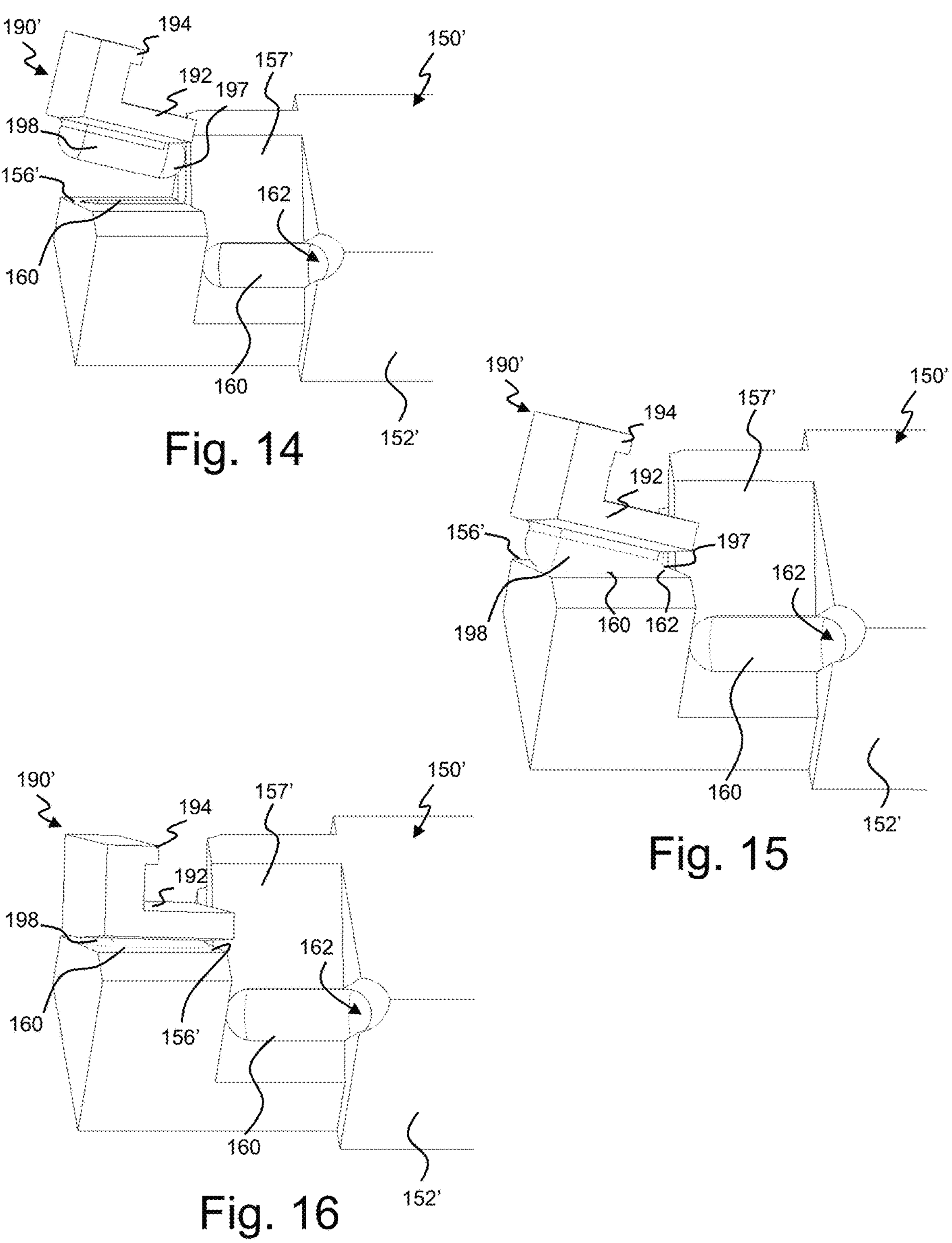
FIGS. 14-16 are expanded perspective views of a portion of an alternative actuator showing the sequential mounting of an alternative pivot member relative thereto.

Referring to FIGS. 14-16, an alternative method of pivotally connecting the pivot members to the actuators will be described. While the figures show a posterior actuator 150', a similar construction may be provided for the anterior actuator. In the present embodiment, each of the ramps 156, 157 defines a pivot slot 160 with a portion 162 that extends laterally under a portion of the actuator body 152'. Instead of a pivot pin slot, each pivot member 190' has a rounded underside member 198 with an extending portion 197. The rounded underside member 198 fits into the pivot slot 160 with the extending portion 197 fitting into the portion 162 that extends laterally under a portion of the actuator body 152'. When fully placed as illustrated in FIG. 16, the pivot member 190' is retained in the actuator and is pivotal thereto.

The pivot members 190, 200 are pivotally connected to and thereby move with the respective actuator 150, 170 while also being engaged with the grooves 117, 119, 137, 139 in the upper and lower end plates 110, 130. As such, as the actuators 150, 170 are moved anteriorly or posteriorly, the pivot members 190, 200 slide along the ramps 116, 118, 136, 138 causing the end plates 110, 130 to move toward or away from one another. The pivoting nature of the pivot members 190, 200 allows the angle between the plates 110, 130 to be changed while maintaining the sliding relationship.

Figures 8, 9:
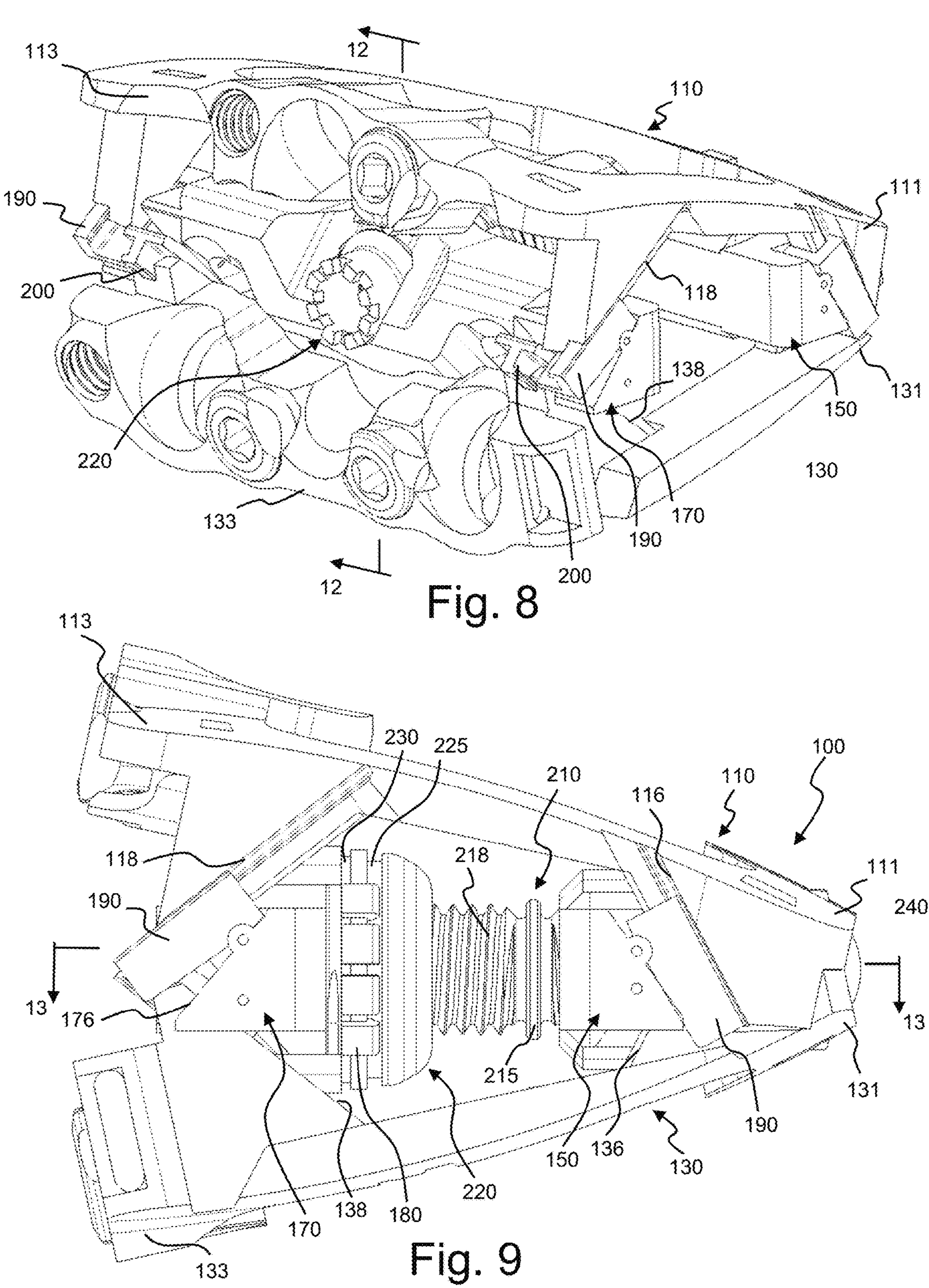
FIG. 8 is a perspective view of the implant of FIG. 1 in an expanded anterior or increased lordotic angle configuration.
FIG. 9 is a side elevation view of the implant as shown in FIG. 8.

Movement of the actuators 150, 170 and the corresponding movement of the end plates 110, 130 will now be described. FIGS. 2 and 3 illustrate the end plates 110, 130 in the collapsed state and the actuators 150, 170 are both generally centrally located. To move the end plates 110, 130 to the expanded state, the anterior actuator 150 moves anteriorly and the posterior actuator 170 moves posteriorly, as shown in FIGS. 4 and 5. As the actuators 150, 170 move, the pivot members 190, 200 slide along the respective ramps 116, 118, 136, 138. In such expanding actuation, the actuators 150, 170 are moved at the same rate and therefore the end plates 110, 130 maintain the given angle between them and the pivot members 190, 200 generally do not pivot. If it is desired to increase the lordotic angle between the plates 110, 130, the anterior actuator 170 is moved anteriorly while the posterior actuator 150 remains stationary, as illustrated in FIGS. 8 and 9. As the anterior actuator 170 moves, the pivot members 190, 200 slide along the respective ramps 118, 138.

Figure 10:
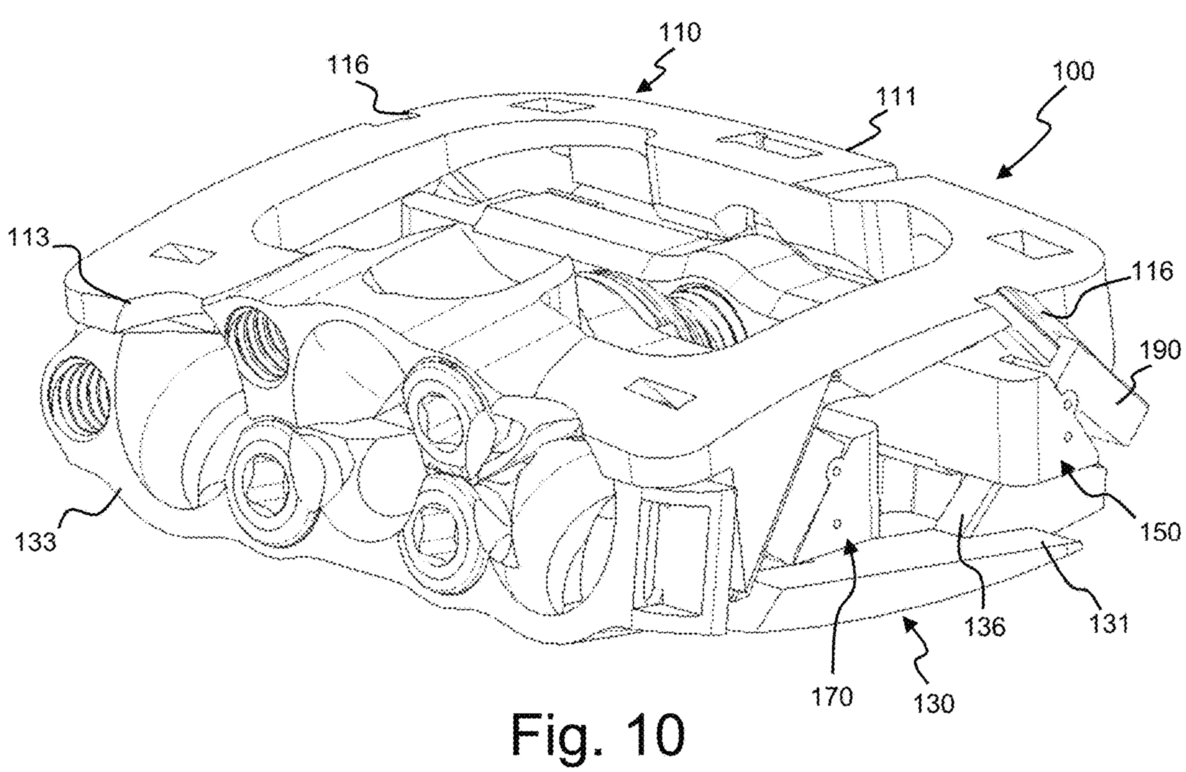
FIG. 10 is a perspective view of the implant of FIG. 1 in an expanded superior or decreased lordotic angle configuration.
Figure 11:
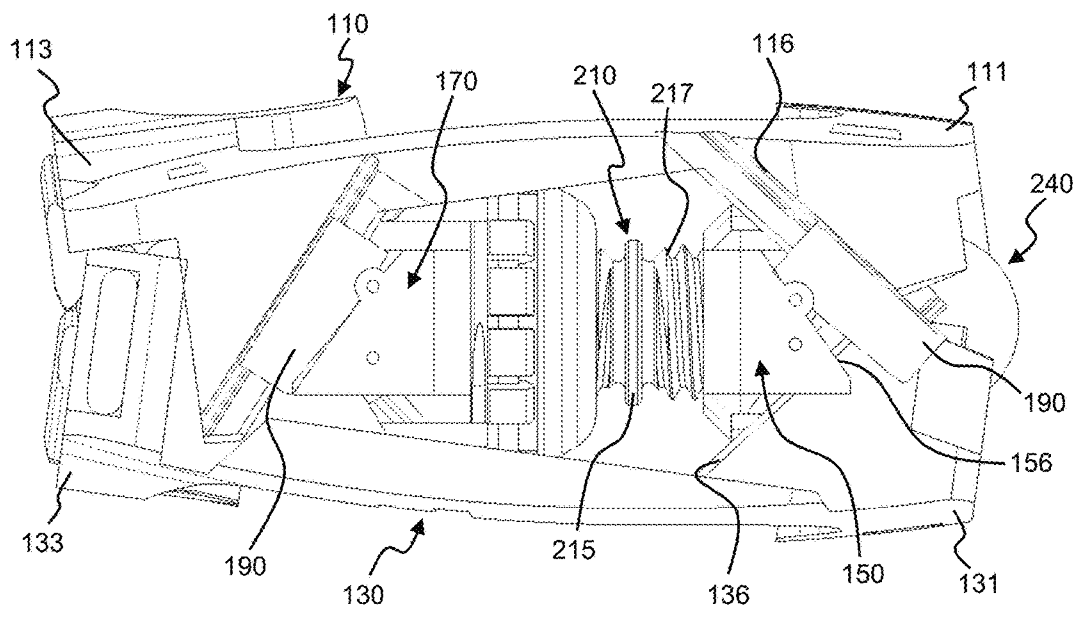
FIG. 11 is a side elevation view of the implant as shown in FIG. 10.

Additionally, because the angle between the end plates 110, 130 changes, each of the pivot members 190, 200 pivots relative to its respective actuator 150, 170. Conversely, if it is desired to decrease the lordotic angle between the plates 110, 130, the posterior actuator 150 is moved posteriorly while the anterior actuator 170 remains stationary, as illustrated in FIGS. 10 and 11. As the posterior actuator 150 moves, the pivot members 190 slide along the respective ramps 116, 136. Again, because the angle between the end plates 110, 130 changes, each of the pivot members 190, 200 pivots relative to its respective actuator 150, 170.

Figures 12, 13:
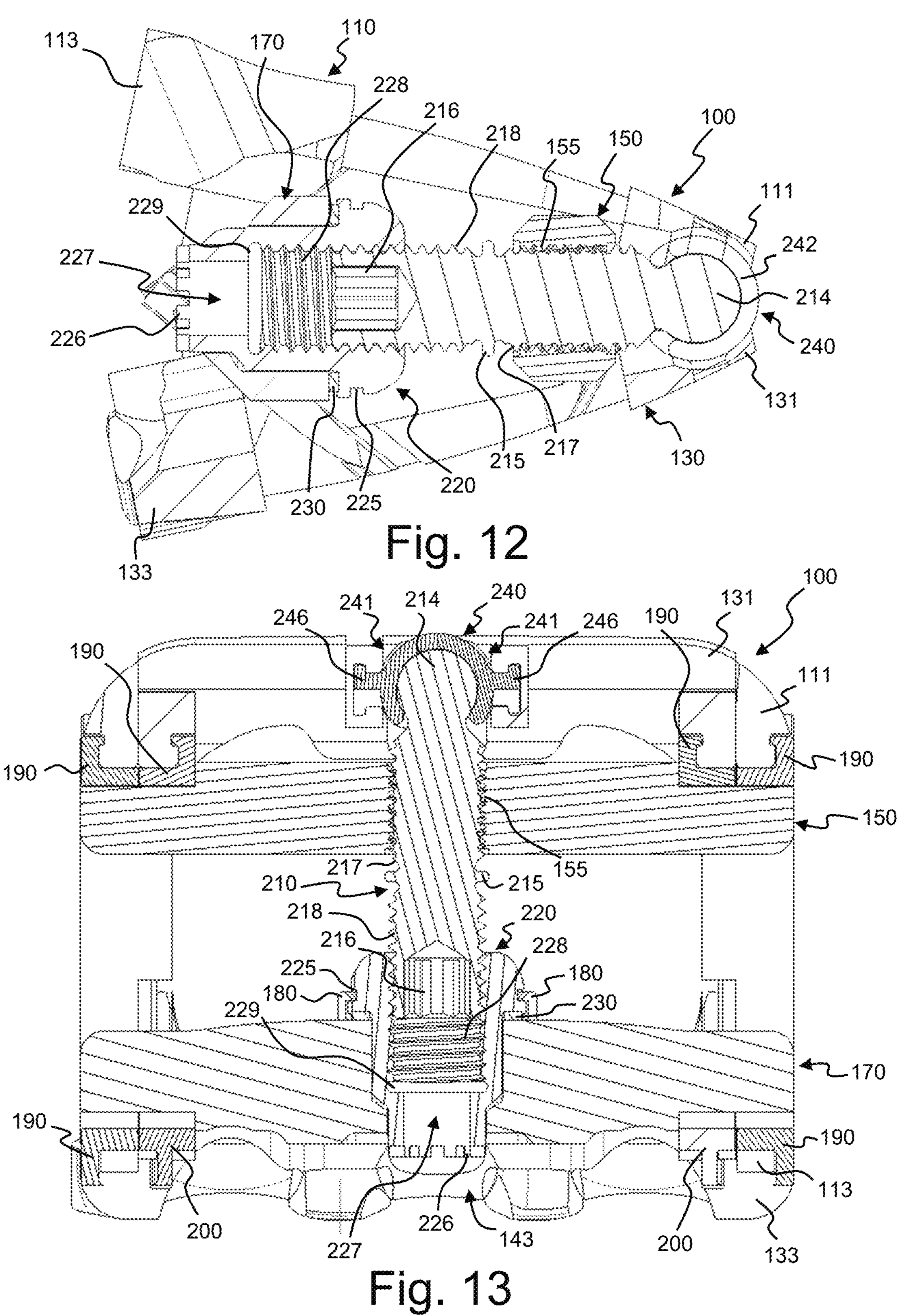
FIG. 12 is a cross-sectional view along the line 12-12 in FIG. 8.
FIG. 13 is a cross-sectional view along the line 12-12 in FIG. 9.

To facilitate movement of the actuators 150, 170, an actuator assembly extends between the actuators 150, 170. Referring to FIGS. 1, 12 and 13, in the present embodiment, the actuator assembly includes an actuator screw 210, an actuator nut 220, and a spherical bearing 240. The actuator screw 210 includes a shaft extending between a posterior end 211 and an anterior end 213. The posterior end 211 of the screw 210 has a ball 214 while the anterior end 213 includes a driver receiver 216. The actuator screw 210 has a first set of threads 217 on the anterior end and a second set of threads 218 on the posterior end with a flange 215 in between. The first and second sets of threads 217, 218 are oppositely handed, i.e. one set is right handed while the other set is left handed. The posterior end 211 of the actuator screw 210 extends through the central through passage 154 of the posterior actuator 150 with the with threads 217 engaged with the internal threads 155.

The ball 214 of the actuator screw 210 extends beyond the posterior actuator 150 and is retained in the spherical bearing 240. In the present embodiment, the spherical bearing 240 is defined by opposed bearing members 241. With reference to FIG. 1, each bearing member 241 has a generally hemispherical bearing surface 242. An arm 244 extends between the bearing surface 242 and a mounting flange 246. Each mounting flange 246 is configured to be received in a respective receiving slot 126, 146 of the upper end plate 110 or the lower end plate 130. With the ball 214 retained between the bearing surfaces 242 and the flanges 246 engaged with the respective end plates 110, 130, the actuator screw 210 is axially fixed relative to the end plates 110, 130 but is free to pivot relative thereto. As such, as the posterior actuator 150 moves along the thread set 217 of the actuator screw 210, the posterior actuator 150 moves relative to the end plates 110, 130.

The actuator nut 220 has a body 222 extending between a posterior end 221 and an anterior end 223. A through passage 227 extends through the body 222 from the anterior end 223 to the posterior end 221. A portion of through passage 227 defines internal threads 228 which are configured to threadably engage the second thread set 218 of the actuator screw 210. A shoulder 229 is defined within the through passage 227 to define a stop for the actuator screw 210. The anterior end 223 of the actuator nut 220 defines a driver engagement 226 about the through passage 227, which in the illustrated embodiment is a series of notches and teeth.

The anterior end 223 of the body 222 of the actuator nut 220 is configured to be received into the non-threaded through passage 174 of the anterior actuator 170. A radial flange 224 extending from the body 222 limits the extent the actuator nut 220 moves into the non-threaded through passage 174. A thrust washer 230 may be positioned between the flange 224 and the anterior actuator 170. A groove 225 is defined in the actuator nut body 222 posteriorly of the flange 224. The fingers 180 extending from the anterior actuator 170 are configured to engage the groove 225 such that the actuator nut 220 is connected to the anterior actuator 170.

The actuator assembly provides three modes of operation. In the first mode of operation, the actuator screw 210 is turned via the driver receiver 216 while the actuator nut 220 is not turned. Engagement of the internal threads 155 of posterior actuator 150 with the first set of threads 217 of the turning actuator screw 210 causes the posterior actuator 150 to move, for example posteriorly. At the same time, since the opposite handed threads 218 of the turning actuator screw 210 are engaging the internal threads 218 of the non-turning actuator nut 220, the actuator nut 220, and thereby the anterior actuator 170, are caused to move in the opposite direction, in this example, anteriorly. This results in both actuators 150, 170 moving toward the ends of the end plates 110, 130 and gives linear expansion with both endplates 110, 130 expanding the same distance (FIGS. 4 and 5). Turning the actuator screw 210 in the opposite direction would move the end plates 110, 130 toward one another.

In the second mode of operation, the actuator screw 210 is not turned while the actuator nut 220 is turned via the driver engagement 226. Since the actuator screw 210 is not turning, the posterior actuator 150 does not move. However, as the actuator nut 220 turns relative to the thread set 218 of the stationary actuator screw 210, the actuator nut 220, and thereby the anterior actuator 170, move alone which expands the anterior end of each endplate only and results in an increase in lordotic angle. (FIGS. 8 and 9). Turning the actuator nut 220 in the opposite direction would move the anterior ends of end plates 110, 130 toward one another.

In the third mode of operation, the actuator screw 210 is turned via the driver receiver 216 while the actuator nut 220 is also turned via the driver engagement 226. Since the actuator screw 210 and the actuator nut 220 are turning at the same rate, there is no relative movement between the actuator nut 220 and the actuator screw 210. As such, the anterior actuator 170 does not move. However, the turning actuator screw 210 causes the posterior actuator 150 to move alone which expands the posterior end of each endplate only and results in a reduction in lordosis. (FIGS. 10 and 11). Turning the actuator screw and actuator nut 220 simultaneously in the opposite direction would move the posterior ends of end plates 110, 130 toward one another.

Devices of the disclosure provide for adjacent vertebrae to be supported during flexion/extension, lateral bending, and axial rotation. In one embodiment, implant 100 is indicated for spinal arthroplasty in treating skeletally mature patients with degenerative disc disease, primary or recurrent disc herniation, spinal stenosis, or spondylosis in the lumbosacral spine (LI-SI). Degenerative disc disease is advantageously defined as discogenic back pain with degeneration of the disc confirmed by patient history and radiographic studies, with or without leg (radicular) pain. Patients may be advantageously treated, for example, who may have spondylolisthesis up to grade 1 at the involved level. The surgery position implant 100 may be performed through an anterior, anterolateral, posterolateral, and/or lateral approach. Various implant methods are disclosed in US 2014/0277489, the contents of which are incorporated herein by reference in its entirety for all purposes. During implantation, the driver receiver 216 and driver engagement 226 may be engaged by separate tools or an integrated tool to actuate the actuator assembly.

While the present disclosure has been described in terms of exemplary aspects, those skilled in the art will recognize that the present disclosure can be practiced with modifications in the spirit and scope of the appended claims. These examples given above are merely illustrative and are not meant to be an exhaustive list of all possible designs, aspects, applications or modifications of the present disclosure.

What is claimed is:

1. A method of stabilizing bones of a joint comprising:

providing an implant for therapeutically separating bones of a joint, the implant comprising:

a first end plate having a bone engaging surface;

a second end plate having a bone engaging surface and disposed to face the first end plate;

an actuator positioned between the first and second end plates;

a pivot member positioned between the first end plate and the actuator to allow the first end plate to slide and pivot against the actuator;

a drive assembly having an actuator screw coupled to the actuator and configured to translate the actuator to cause the first end plate to vertically rise relative to the second end plate, and pivoting of the pivot member allowing an angle between the first and second end plates to change, positioning the implant between adjacent bones of the joint; and rotating the actuator to move the first end plate relative to the second end plate to move the first and second endplates farther apart to separate bones of the joint.

2. The method of claim 1, wherein:

the pivot member has a laterally extending flange; and the first end plate has a groove that receives the laterally extending flange to prevent separation of the pivot member from the first end plate.

3. The method of claim 1, wherein:

the actuator has a rounded recess; and the pivot member has a rounded underside received in the rounded recess for pivoting about the rounded recess.

4. The method of claim 1, wherein:

the actuator has a rounded recess;

the pivot member has a laterally extending flange and a rounded underside received in the rounded recess for pivoting about the rounded recess; and the first end plate has a groove that receives the laterally extending flange to prevent separation of the pivot member from the first end plate.

5. The method of claim 1, wherein the drive assembly includes:

an actuator screw threadably coupled to internal threading in the actuator; and an actuator nut with a through passage defining an internal threading, the internal threading threadably engaged with the external threading of the actuator screw.

6. The method of claim 5, further comprising a spherical bearing positioned between the first and second end plates, wherein the actuator screw includes a ball-shaped end received in the spherical bearing.

7. The method of claim 6, wherein the other end of the actuator screw includes a drive feature for receiving a driver for rotation of the actuator screw.

8. The method of claim 7, further comprising a second actuator spaced from the actuator, wherein the actuator nut includes a body with a radial flange extending outwardly, wherein at least a part of the body of the actuator nut is received in a through passage defined in the second actuator.

9. The method of claim 8, wherein an anterior end of the body of the actuator nut defines a driver engagement about the through passage of the actuator nut.

10. The method of claim 9, further comprising a thrust washer positioned between the radial flange and the second actuator.

11. A method of stabilizing bones of a joint comprising:

providing an implant, the implant comprising:

a first end plate having a bone engaging surface and having a ramped surface;

a second end plate disposed to face the first end plate and having a bone engaging surface and a ramped surface;

an actuator positioned between the first and second end plates and having a through passage;

a first pivot member pivotally coupled to the actuator and in sliding engagement with the ramped surface of the first end plate;

a second pivot member pivotally coupled to the actuator and in sliding engagement with the ramped surface of the second end plate;

a drive assembly having an actuator screw threadably coupled to internal threading in the actuator and configured to translate the actuator by rotation, the translation of the actuator causing the first and second pivot members to slide against the ramped surfaces of the respective first and second end plates to cause the first end plate to vertically rise relative to the second end plate, the pivot members adapted to pivot to allow an angle between the first and second end plates to change, positioning the implant between adjacent bones of a joint; and rotating the actuator to move the first end plate relative to the second end plate to move the first and second endplates farther apart to separate bones of the joint.

12. The method of claim 11, wherein:

the first pivot member has a laterally extending flange; and the first end plate has a groove that receives the laterally extending flange to prevent separation of the first pivot member from the first end plate.

13. The method of claim 11, wherein:

the actuator has a rounded recess; and the first pivot member has a rounded underside received in the rounded recess for pivoting about the rounded recess.

14. The method of claim 11, wherein:

the actuator has a rounded recess;

the first pivot member has a laterally extending flange and a rounded underside received in the rounded recess for pivoting about the rounded recess; and the first end plate has a groove that receives the laterally extending flange to prevent separation of the first pivot member from the first end plate.

15. The method of claim 11, wherein the drive assembly includes an actuator nut having internal threading engaging the external threading of the actuator screw.

16. The method of claim 15, further comprising a spherical bearing positioned between the first and second end plates, wherein the actuator screw includes a ball-shaped end received in the spherical bearing.

17. The method of claim 16, wherein the other end of the actuator screw includes a drive feature for receiving a driver for rotation of the actuator screw.

18. The method of claim 17, further comprising a second actuator spaced from the actuator, wherein the actuator nut includes a body with a radial flange extending outwardly, wherein at least a part of the body of the actuator nut is received in a through passage defined in the second actuator.

19. The method of claim 18, wherein an anterior end of the body of the actuator nut defines a driver engagement about the through passage of the actuator nut.

20. The method of claim 19, further comprising a thrust washer positioned between the radial flange and the second actuator.

* * * * *